United States Patent
Thurk et al.

(10) Patent No.: US 7,423,021 B2
(45) Date of Patent: *Sep. 9, 2008

(54) PEPTIDIC THROMBIN INHIBITORS

(75) Inventors: Marcel Thurk, Bovenden (DE); Andreas Schwienhorst, Gottingen (DE)

(73) Assignee: NSCI Novel Science International GmbH, Goettingen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/542,519

(22) PCT Filed: Jan. 15, 2004

(86) PCT No.: PCT/EP2004/000256

§ 371 (c)(1), (2), (4) Date: Oct. 21, 2005

(87) PCT Pub. No.: WO2004/063212

PCT Pub. Date: Jul. 29, 2004

(65) Prior Publication Data

US 2006/0105959 A1 May 18, 2006

(30) Foreign Application Priority Data

Jan. 15, 2003 (DE) ................. 103 01 255

(51) Int. Cl.
*A61K 38/08* (2006.01)
*C07K 7/04* (2006.01)
*A61K 38/00* (2006.01)
*A61K 38/02* (2006.01)
*C07K 2/00* (2006.01)
*C07K 1/00* (2006.01)

(52) U.S. Cl. ............................. 514/17; 514/2; 530/300; 530/329; 530/333

(58) Field of Classification Search ........................ None
See application file for complete search history.

(56) References Cited

U.S. PATENT DOCUMENTS

| 3,826,794 | A | 7/1974 | Flouret |
| 4,654,302 | A | 3/1987 | Fritz et al. |
| 5,433,940 | A | 7/1995 | Maraganore et al. |
| 7,081,447 | B2 * | 7/2006 | Thurk ........................ 514/17 |

FOREIGN PATENT DOCUMENTS

| EP | 168342 | 1/1986 |
| EP | 171024 | 2/1986 |
| EP | 200655 | 11/1986 |
| WO | WO-03/022873 A1 | 3/2003 |

OTHER PUBLICATIONS

R.J. Bastin, et al. Org. Proc. Res. Develop. (2000) 4, pp. 427-435.*
English equivalent for claims of WO 03/022873 A1 (pp. 49-73).*
Claeson, G.; "Synthetic Peptides and Peptidomimetics as Substrates and Inhibitors of Thrombin and Other Proteases in the Blood Coagulation System"; Blood Coagulation & Fibrinolysis, Rapid Communications, Oxford, GB, vol. 5, 1994, pp. 411-436.
Kamphausen, Stefan, et al.; "Genetic algorithm for the design of molecules with desired properties"; Journal of Computer-Aided Molecular Design, vol. 16, No. 8-9, 2002, pp. 551-567.
Stone, Stuart R. & Hofsteenge, Jan, "Kinetics of the Inhibition of Thrombin by Hirudin." Biochemistry, 1986, vol. 25, pp. 4622-4628.
Markwardt, F., et al., "Pharmacological Studies on the Antithrombotic Action of Hirudin in Experimental Animals." From the Institute of Pharmacology and Toxicology, Medical Acadamy Erfurt, Erfurt, G.D.R., 1982, pp. 226-229.
Harvey, R.P., et al. "Cloning and Expression of a cDNA Coding for the Anticoagulant Hirudin From the Bloodsucking Leech, *Hirudo Medicinalis*." Proc. Natl. Acad. Sci., Feb. 1986, vol. 83, pp. 1084-1088.
Wirsching, Frank, et al. "Display of Functional Thrombin Inhibitor Hirudin on the Surface of Phage M13." Gene 204, 1997, p. 177-184.
Bergmann, Cornelia, et al. "Chemical Synthesis and Expression of a Gene Coding for Hirudin, the Thrombin-Specific Inhibitor From the Leech *Hirudo Medicinalis*." Biol. Chem. Hoppe-Seyler, Aug. 1968, vol. 367, p. 731-740.
Shuman, Robert T., et al. "Highly Selective Tripeptide Thrombin Inhibitors." Journal of Med. Chem., 1993, vol. 36, p. 314-319.
Blomback, B., et al. "Synthetic Peptides with Anticoagulant and Vasodilating Activity." Scan. J. Clin. Lab. Invest. Suppl., 1969, vol. 107, p. 59-64.
Bajusz, S., et al. "Inhibition of Thrombin and Trypsin by Tripeptide Aldehydes." Int. J. Peptide Protein Res., 1978, vol. 12, p. 217-221.
Kettner & Shaw, "D-PHE-PRO-ARGCH$_2$Cl-A Selective Affinity Label for Thrombin." Thrombosis Research, 1979, vol. 14, p. 969-973.

* cited by examiner

*Primary Examiner*—Andrew D. Kosar
(74) *Attorney, Agent, or Firm*—Darby & Darby PC

(57) ABSTRACT

The invention relates to biologically active molecules, which interact with and inhibit thrombin. The invention particularly relates to molecules of general formula (I): $Y^1$—(NH—$X^1$—CO)—(NH—$X^2$—C=O)—(NH—$X^3$—C=O)—(NH—$X^4$—C=O)—(NH—$X^5$—C=O)(NH—$X^6$—C=O)—$Y^2$, wherein the compound can be used for thrombin inhibition, inhibition of fibrin formation, and/or for the inhibition of the formation of a clot. Compounds disclosed herein can also be used for treatingm, diagnosing, and prophylaxis of thrombotic disorders.

16 Claims, No Drawings

PEPTIDIC THROMBIN INHIBITORS

This invention relates to biologically active substances which interact with thrombin and inhibit it. The substances are useful as anticoagulation agents for humans and animals. In particular, this invention extends to small, 3-6 amino acid-long, peptidic molecules of the general formula (I)

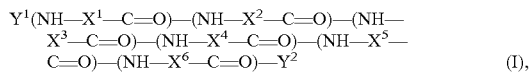

$$Y^1(NH-X^1-C=O)-(NH-X^2-C=O)-(NH-X^3-C=O)-(NH-X^4-C=O)-(NH-X^5-C=O)-(NH-X^6-C=O)-Y^2 \quad (I),$$

in which $Y^1$, $Y^2$, and $X^{1-6}$ have the meaning stated in the description, or are N-terminally or C-terminally shortened variants of the formula (I) with high anti-thrombic activity. The invention also relates to compositions with combinations of these substances for therapeutic, prophylactic, and diagnostic purposes.

Acute vascular diseases such as myocardial infarct, stroke, lung embolism, deep vein thrombosis, peripheral arterial occlusion, and other thromboses in the blood system constitute a significant health risk. Diseases of this type are caused by complete or partial occlusion of the blood vessel by a clot which contains fibrin and blood platelets.

Present methods for the treatment and prophylaxis of such thrombosis diseases include therapeutic agents which act in two different ways. The first type of therapeutic agent prevents the thrombin activity or thrombosis formation and thus the formation of the clot. These medicaments also prevent the development of blood platelets and their aggregation. The second category of medicaments accelerates thrombolysis and dissolves the clot, thus removing it from the blood vessel and releasing the blockage of the blood flow.

Heparin and cumarin, preparations of the first type, are used to a large extent for the treatment of venous thromboembolisms in which thrombin activity is responsible for the development and expansion of the thrombus. Although effective, heparin nonetheless causes many adverse side effects, such as hemorrhaging or thrombocytopenia. The same holds for cumarin which acts by blocking or preventing the formation of prothrombin and needs some time for its full activity to develop. Altogether this has led to a search for specifically acting and less toxic anti-coagulation agents such as, for example, peptidic inhibitors.

Hirudin is a naturally occurring polypeptide which is produced from the leech *Hirudo medicinalis*. This substance, which is synthesized in the salivary gland of the leech, is the most potent known natural coagulation inhibitor. Hirudin is a direct thrombin inhibitor and prevents the coagulation of the blood by a strongly binding to the thrombin ($Kd=2\times10^{-4}$ M) in a stochiometric 1:1 complex [Stone & Hofstenge, Kinetics of the inhibition of thrombin by hirudin, Biochemistry 25, Pages 4622-4628 (1986)]. This in turn prevents the thrombin from catalyzing the conversion of fibrinogen into fibrin (the clot) since it prevents all the other thrombin-mediated cleavage processes.

In animal studies the efficacy of hirudin obtained in purified form from leeches has been demonstrated in the prevention of venous thrombosis, arterial occlusion, and thrombin-induced disseminated intravascular coagulation. Moreover, hirudin shows low toxicity, low antigenicity, and a very short clearance time from the blood circulation [F. Markwardt et al., Pharmacological studies on the anti-thrombic action of hirudin in experimental animals, Thromb. Haemost. 47, Pages 226-229 (1982)]. In projects which are targeted at producing greater amount of hirudin, attempts were made at producing the polypeptide by recombinant DNA technology. The presence of O-sulfated tyrosine residue on natural hirudin and the inability of microorganisms to perform a similar protein modification made the prospect of a recombinant production of biologically active hirudin highly speculative. The observation that desulfated hirudin is almost as active as its sulfated counterpart [U.S. Pat. No. 4,654,302] showed the way to the cloning and expression in various expression systems, among them *S. cerevisiae* [Harvey et al., Cloning and expression of cDNA coding for the anticoagulant hirudin from the bloodsucking leech, *Hirudo medicinalis*. PNAS 83, Pages 1084-1088; European Patent Applications 158 654, 168 342, and 171 024], *E. coli* [Bergmann et al., Chemical synthesis and expression of a gene coding for hirudin, the thrombin-specific inhibitor from the leech, Biol. Chem. Hoppe-Seyler 367, Pages 731-740; European Patent. Application 200 655], and on the tip of a filamentous phage as a fusion protein with protein III (pIII) [Wirsching et al., Display of functional thrombin inhibitor hirudin on the surface of phage M13, Gene 204, Pages 177-184]. Despite these advances, hirudin continues to be rather expensive to produce. Nonetheless, it has run through the third clinical phase and was recently approved for the treatment of heparin-induced thrombocytopenia (HMR).

Just recently, success was achieved in the identification of peptide fragments of natural hirudin which also increase the coagulation time. Such peptide fragments cannot however be seen as completely satisfactory due to their low activity with respect to the prevention of the formation of clots. Thus, for example, N-acetyl-hirudin$_{45-65}$ has an activity that is lower than that of natural hirudin by four orders of magnitudes, although it remains a relatively large molecule. The problem of rather low affinities for thrombin was solved by the development of hirulogs (U.S. Pat. No. 5,433,940). These molecules emulate the activity of hirudin due to the fact that they bind to the anion-binding exosite of low affinity as well as to the catalytic site on the .alpha.-thrombin. From this, hirulogs are characterized by a thrombin anion-binding exosite association moiety, a linker group, and a thrombin catalytic site-directed moiety. The usually preferred hirulog is hirulog-8, a peptide of 20 amino acids which is synthesized from the catalytic site-inhibiting peptide D-Phe-Pro-Arg-Pro- (SEQ ID NO:1), a Gly.sub.4 (SEQ ID NO:2) linker sequence, and the sequence -Asn-Gly-Asp-Phe-Glu-Glu-lle-Pro-Clu-Glu-Tyr-Leu-OH (SEQ ID NO:3) of the hirudin. Hirulog-8 has been on the market in the U.S.A. for a short time.

Despite the advances of relatively high activity for thrombin ($K_i=2.3$ nM), hirulogs are relatively large molecules which must be synthesized in relatively tiresome schemata such as mixed heterologous/solid phases. Like hirudin, hirulogs can only be administered parenterally and must be monitored carefully. Thus, hirulogs are not suitable as chemical leads for small molecules which ultimately could also be administered orally.

Thus, there were several efforts to identify smaller peptides as potent thrombin inhibitors. Already in 1956 Bettelheim showed that fibrinopeptide A comparably inhibits the reaction between thrombin and fibrinogen. In joint research of Blombäck and the Nobel Pharma/Kabi in Stockholm, peptide sequences which are derived from fibrinopeptide A, have no more than nine amino acids, and have good activity for thrombin were found. Significant contributors to the activity were an N-terminal Phe and a C-terminal Arg, separated by seven amino acids. Fewer amino acids reduced the activity but astonishingly a tripeptide with N-terminal and C-terminal Phe or Arg exhibited excellent activity. The best tripeptide with inhibiting activity on the thrombin-fibrinogen reaction was Bz-Phe-Val-Arg-OMe, where Val precedes the Arg as in the full-length fibrinopeptide [Blombäck et al., Synthetic peptides with anticoagulant and vaodilating [sic] activity, Scand. J. Clin. Lab. Invest. 24, Pages 59-66 (1969), U.S. Pat. No. 3,826,794 (1974)]. In contradistinction to the fibrinopeptide A, Pro precedes the Arg in one series of other thrombin extract regions, such as that of prothrombin, of factor XIII, and the human growth hormone. Most of the presently most active thrombin-inhibiting peptides and peptidomimetic agents were developed on the basis of the Pro-Arg sequence. Among these most active inhibitors are H-D-Phe-Pro-Arg-H ($K_i$=70 nM), [Bajuz et al., Inhibition of thrombin and trypsin by tripeptide aldehydes, Int. J. Peptide Protein Res. 12, Pages 217-221 (1978); Hung. Pat. 169870 (1974)]. The idea for this peptide aldehyde grew from the discovery of peptide aldehydes of bacterial origin by H. Umezawa. These so-called leupeptides (for example, Ac-Leu-Leu-Arg-H) are inhibitors of plasmin and other trypsin-like proteases but not of thrombin. The aldehyde-carbon has in its acetal form a tetrahedral structure, the same as the carbonyl-carbon of the substrate in the transition phase.

From these just mentioned aldehydes, Shaw et al. synthesized the irreversible chloromethylketone inhibitor H-D-Phe-Pro-Arg-$CH_2$-Cl with a $K_i$ of 25 nM [Kettner et al., H-D-Phe-Pro-Arg-$CH_2$-Cl-a selective activity label for thrombin, Thromb. Res. 14, Pages 969-973 (1979)]. Developmental work at Eli Lilly led to N-methyl-D-Phe-Pro-Arg-H, also known as efegatran. The D-Phe-Pro-Arg sequence has recently been developed still further. Speculations that an N-terminal amino acid with aromatic/lipophilic groups could yield greater activity with respect to thrombin led to the discovery of several inhibitors with new amino acids at this position, among them β-β-diphenylalanine (Dpa), phenylglycine, cyclohexylglycine, carboxy-1, 2, 3, 4-tetrahydroisoquinoline (Tiq) [Schuman et al., Highly selective thrombin inhibitors. J. Med. Chem. 36, Pages 314-319 (1993)]. The most interesting compound was D-1-Tiq-Pro-Arg-H, which yielded twice the gain in activity compared to that of Boc-D-Phe-Pro-Arg-H. However, trypsin is inhibited to the same degree as thrombin.

From the data accessible today it is clear that, although there are several effective anti-coagulation compounds, there is a need for high-performance anti-thrombin agents which act quickly to prevent the formation of clots and which do not interfere with other protease activities, e.g. plasmin action in dissolving the clot.

Starting from this state of the art, the objective of the present invention is to provide compounds which are biologically active in the sense of thrombin inhibition and avoid the disadvantages of the previously described state of the art. The problem underlying the invention consisted moreover of inhibiting thrombin specifically with low concentrations of the active ingredient and low cell toxicity.

According to the invention this objective is realized by a compound of the formula

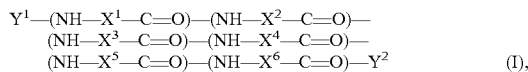

where $Y^1$ is either
1. a hydrogen atom or
2. a methyl group or
3. an acetyl group or
4. is characterized by a backbone of a chain of 1 to 32 carbon atoms where (NH—$X^1$—C=O) is a D-amino acid or L-amino acid, preferably
1. valine or
2. alanine or
3. leucine or
4. isoleucine or
5. norleucine or
6. asparagine or
7. glutamine or
8. serine or
9. threonine or
10. tyrosine or
11. arginine or
12. lysine or
13. ornithine or
14. phenylalanine or
15. dichlorophenylalanine or
16. tetrahydronorharman-3-carboxylic acid or
17. tetrahydroisoquinoline(1, 2, 3, 4)-3-carboxylic acid or
18. 4-phenylpiperidine-4-carboxylic acid or
19. thienylalanine or
20. phenylglycine or
21. p-nitrophenylalanine or
22. tranexamic acid (=trans-4-(aminomethyl)cyclohexanecarboxylic acid) or
23. trans-4-(guanidinomethyl)cyclohexanecarboxylic acid or
24. is replaced by a chemical bond, where (NH—$X^2$—C=O) is a D-amino acid or L-amino acid, preferably
1. alanine or
2. valine or
3. leucine or
4. isoleucine or
5. norleucine or
6. serine or
7. threonine or
8. tyrosine or
9. proline or
10. citrullin or
11. arginine or
12. lysine or
13. ornithine or
14. histidine or
15. glutamic acid or
16. aspartic acid or
17. tryptophan or
18. cyclohexylalanine or
19. cyclohexylglycine or
20. is replaced by a chemical bond, where (NH—$X^3$—C=O) is any amino acid, for example,
1. L-cyclohexylalanine or
2. D-cyclohexylalanine or
3. L-cyclohexylglycine or
4. D-cyclohexylglycine or where (NH—$X^4$—C=O) is a small amino acid, preferably
1. L-proline or
2. D-proline or
3. L-azetidine-2-carboxylic acid or
4. D-azetidine-2-carboxylic acid, where (NH—$X^5$—C=O) is a preferably aromatic amino acid, such as
1. L-tyrosine or
2. D-tyrosine or
3. L-phenylalanine or
4. D-phenylalanine, where (NH—$X^6$—C=O) is an amino acid with a basic side chain, preferably
1. L-arginine or
2. D-arginine or
3. L-lysine or
4. D-lysine or
5. L-ornithine or
6. D-ornithine or
7. L-homoarginine or 8. D-homoarginine, where $Y^2$ is either
1. an OH group (the C-terminal amino acid has a terminal carboxylic acid group) or
2. an amino group (in the C-terminal amino acid the carboxylic acid is replaced by an amide group) or
3. a hydrogen atom (in the C-terminal amino acid the carboxylic acid is replaced by an aldehyde group) or
4. 7-amido-4-methylcumarin (combined via the carboxylic acid group) or
5. paranitroanilide (combined via the carboxylic acid group) or
6. is replaced by a compound chain of 1 to 35 atoms, or a molecule shortened at the C-terminus and/or at the N-terminus by not less than one amino acid and pharmaceutically acceptable salts thereof.

The invention also relates to derivatives of the aforementioned compounds.

Particularly advantageous results are achieved if the peptide according to the invention is N-acetyl-$R_1$-L-Cha-D-Pro-D-Tyr-L-Arg-amide, where $R_1$ stands for D-Gln-D-His, D-Glu, D-Val-D-His, L-Ala, L-Ile-L-Arg, L-Tyr-L-Cit, L-Ser-L-Ser, D-Val, L-Trp, L-Ser-L-Ala, L-Ser-L-Arg, D-Lys-L-Nle, D-TYr, L-Arg, or L-Tyr-D-Pro if the peptide according to the invention is N-acetyl-L-Ala-D-Cha-L-Aze-D-Tyr-L-Arg amide, N-acetyl-L-Ala-D-Cha-L-Pro-D-Tyr-L-Har amide, or N-acetyl-$R_2$-D-Cha-L-Aze-D-Tyr-L-Har amide, where $R_2$ stands for L-Trp, L-Ala, D-Phe, L-Dcp, L-Nhm, L-Iq3, L-Ppd, L-Tea, L-Phg, L-Nle, L-Cha, or L-Pnp.

The compounds according to the invention can be used to inhibit all thrombin-mediated or thrombin-associated functions and processes. Pharmaceutical compositions which contain these compounds, as well as methods for the treatment and prophylaxis of vascular diseases, inflammatory reactions, carcinomas, and neurodegenerative diseases which use these compounds, are also the object of the invention. The compounds can also be used for ex-vivo expression, for storage and treatment of blood outside of the body, and for coating of invasive devices. Furthermore, the compounds can be administered to a patient (by patient a person or an animal is understood here) in combination with a fibrinolytic agent in order to increase the activity of a given dose or to reduce the dose necessary to achieve a desired effect, such as dissolving a blood clot or the prevention of the re-occlusion of the previously blocked blood vessel.

Due to their high potential and the fact that they can be produced by chemical synthesis technologies, the compounds can be produced economically in commercially practical amounts. The peptides are converted into suitable salt forms such as acetates and sulfates.

Moreover, the molecules according to the invention are significantly smaller than hirudin and the other previously described peptidic thrombin inhibitors. Thus, causing an adverse reaction of the immune system in patients treated with these substances is less likely. Accordingly, the use of these thrombin inhibitors is not restricted to the treatment of acute diseases. These compounds can also be used in therapy of chronic thromboembolitic diseases such as arteriosclerosis or restenosis as a consequence of an angioplasty. The compounds according to the invention can also be used in a plurality of other applications instead of natural and recombinant thrombin.

As can be seen from the disclosure, the compounds, compositions, and processes according to the invention are useful for the treatment and care of various diseases in connection with adverse effects of thrombin, as well as for diagnostic purposes.

Finally it should be mentioned that the molecules of this invention can serve as a chemical lead for the development of molecules with still more advantageous properties in regard to the aforementioned applications.

Pharmaceutically acceptable salts of peptides of this invention contain the salts produced by the addition of acid, said salts being formed from inorganic acids and carboxylic acids. The compounds which are represented by the formula (I) are produced by known methods of peptide coupling.

In a preferred form of embodiment the compounds according to the invention are present as a mixture of compounds which is characterized by its content in at least two of the compounds according to the invention. Preferred pharmaceutically acceptable salts of the compounds are formed with an inorganic acid. In so doing, the formation of a pharmaceutically acceptable salt with hydrochloric acid, chloric acid, hydrobromic acid, bromic acid, and/or another halogen acid is particularly preferred. Another particularly preferred form of embodiment consists of the formation of a pharmaceutically acceptable salt with sulfuric acid and/or phosphoric acid. Advantageously a pharmaceutically acceptable salt can also be formed with an organic acid In so doing, the formation of the pharmaceutically acceptable salt with acetic acid, propionic acid, malonic acid, maleic acid, citric acid, succinic acid, fumaric acid, malic acid, benzoic acid, and/or a similar carboxylic acid is particularly preferred. The salts formed by the addition of salt are produced in a conventional manner, for example, by neutralizing the free base form of the compound (I) with the acid.

The substances according to the compound can be used in compounds and methods for the inhibition of all the thrombin-mediated or thrombin-associated functions. Pharmaceutical compositions which contain these molecules, as well as methods for the treatment and prophylaxis of vascular diseases, inflammatory reactions, carcinomas, and neurodegenerative diseases which use these compounds, are also part of the invention. The compounds can also be used for ex-vivo expression, for storage and treatment of blood outside of the body, and for coating of invasive devices. Furthermore, the compounds according to the invention can be administered to a patient (by patient, a person or an animal is understood here) in combination with a fibrinolytic agent in order to increase the activity of a given dose or to reduce the dose necessary to achieve a desired effect, such as dissolving a blood clot or the prevention of the re-occlusion of a previously blocked blood vessel.

Due to their high potential and the fact that they can be produced by chemical synthesis technologies, the substances according to the invention can be produced economically in commercially practical amounts. The peptides are converted into suitable salt forms such as acetates and sulfates.

The invention also relates to a drug which is characterized by its content in one or more compounds according to the invention with the customary carrier substances, adjuvants, or additives. Furthermore a diagnostic composition with a content of one or more compounds is also the object of the invention.

An additional object of the invention consists of the use of the compound as a thrombin inhibitor as well as for the production of a drug for thrombin inhibition, inhibition of fibrin formation, and/or for the inhibition of the formation of a clot.

The use of one or more compounds for the production of a diagnostic composition is also the object of the invention. In one of the particularly preferred forms of embodiment a compound according to the invention is used for the production of a diagnostic composition, where in the formula (I) $Y^2$ is 7-amido-4-methylcumarin or paranitroanilide.

The compounds according to the invention exhibit numerous advantages with respect tot the previously known thrombin inhibitors. In particular the peptides are easy to synthesize, active even when slightly modified, and exhibit a high activity with simultaneously high specificity and low toxicity. Moreover, the small peptides serve, unlike hirudin and hirulog, as chemical leads for active substances which preferably can be administered orally.

The following examples are intended to explain the invention without restricting it.

EXAMPLE 1

N-acetyl-D-Gln-D-His-L-Cha-D-Pro-D-Tyr-L-Arg amide

This peptide was produced by a solid-phase synthesis with the aid of a ABIMED synthesizer AMS 96 (ABIMED Analysen-Technik GmbH, Langenfeld, Germany). In detail 1 mEq of Rink amide resin is allowed to react sequentially with 2×5 mEq of protected amino acid. The activation was done with 2×5 mEq of TBTU (O-benzotriazol-1-yl)-N,N,N',N'-tetramethyluroniumtetrafluoroborate. After up to 6 cycles of the synthesis the N-terminus was acetylated with acetic acid anhydride. Then the protection of the peptide was removed by a treatment with 90% TFA, 2.5% triisopropylsilane, 2.5% $H_2O$, and 5% dichloromethane. The decoupling of the peptide from its carrier was done in the same step. In a drying step the test compound was subsequently partially dissolved in 20 µl of trifluoroacetic acid and then incubated with 2×750 µl of cold butyl ether at 20° C. After centrifugation the excess was removed and the remaining ether evaporated. The identity of the products was confirmed by random sample by mass spectroscopy.

The inhibition of the thrombin was determined by in-vitro inhibition of the amidase activity of the thrombin and is 59% with a peptide concentration of 1 µM. The values of the inhibiting constants $K_i$ were obtained from assays in which thrombin hydrolyzes the fluorogenic substrate Tos-Gly-Pro-Arg-(7-amino-4-methylcumarin). The assays were carried out in 30 µl of assay buffer (0.05 M tris, 0.1 M NaCl, 0.1% PEG 8000, pH 7.6) with 10 µl of human thrombin solution ($10^{-5}$ U/µl in the assay buffer) and 140 µl of a solution of the fluorogenic substrate in an assay buffer at a concentration of 30 µM. Solutions of the test compound (10 µl) were added at various concentrations. The rates of the hydrolysis of the substrate were measured by monitoring the reactions at 460 nM of the release of 7-amino-4-methylcumarin using AMC. The reaction reached an equilibrium state within three minutes, after thrombin, the substrate, and an inhibitor were mixed. The kinetic data of the competing inhibition ($K_m$, $V_{max}$, and $K_i$) were analyzed by means of the representation according to Hanes (A/V against A at various values of A, where A is the substrate concentration and V the reaction rate).

EXAMPLE 2

N-acetyl-D-Glu-L-Cha-D-Pro-D-Tyr-L-Arg amide

This peptide was synthesized as described in example 1 and prepared for use in the assay.

The inhibition of thrombin was determined by in-vitro inhibition of the amidase activity of the thrombin as in example 1 and is 58% with a peptide concentration of 1 µM.

EXAMPLE 3

N-acetyl-D-Val-D-His-L-Cha-D-Pro-D-Tyr-L-Arg amide

This peptide was synthesized as described in example 1 and prepared for use in the assay.

The inhibition of thrombin was determined by in-vitro inhibition of the amidase activity of the thrombin as in example 1 and is 51% with a peptide concentration of 1 µM.

EXAMPLE 4

N-acetyl-L-Ala-L-Cha-D-Pro-D-Tyr-L-Arg amide

This peptide was synthesized as described in example 1 and prepared for use in the assay.

The inhibition of thrombin was determined by in-vitro inhibition of the amidase activity of the thrombin as in example 1 and is 44% with a peptide concentration of 1 µM.

EXAMPLE 5

N-acetyl-L-Ile-L-Arg-L-Cha-D-Pro-D-Tyr-L-Arg amide

This peptide was synthesized as described in example 1 and prepared for use in the assay.

The inhibition of thrombin was determined by in-vitro inhibition of the amidase activity of the thrombin as in example 1 and is 61% with a peptide concentration of 1 µM.

EXAMPLE 6

N-acetyl-L-Tyr-L-Cit-L-Cha-D-Pro-D-Tyr-L-Arg amide

This peptide was synthesized as described in example 1 and prepared for use in the assay.

The inhibition of thrombin was determined by in-vitro inhibition of the amidase activity of the thrombin as in example 1 and is 55% with a peptide concentration of 1 µM.

EXAMPLE 7

N-acetyl-L-Ser-L-Ser-L-Cha-D-Pro-D-Tyr-L-Arg amide

This peptide was synthesized as described in example 1 and prepared for use in the assay.

The inhibition of thrombin was determined by in-vitro inhibition of the amidase activity of the thrombin as in example 1 and is 40% with a peptide concentration of 1 µM.

EXAMPLE 8

N-acetyl-D-Val-L-Cha-D-Pro-D-Tyr-L-Arg amide

This peptide was synthesized as described in example 1 and prepared for use in the assay.

The inhibition of thrombin was determined by in-vitro inhibition of the amidase activity of the thrombin as in example 1 and is 45% with a peptide concentration of 1 µM.

EXAMPLE 9

N-acetyl-L-Trp-L-Cha-D-Pro-D-Tyr-L-Arg amide

This peptide was synthesized as described in example 1 and prepared for use in the assay.

The inhibition of thrombin was determined by in-vitro inhibition of the amidase activity of the thrombin as in example 1 and is 63% with a peptide concentration of 1 µM.

EXAMPLE 10

N-acetyl-L-Ser-L-Ala-L-Cha-D-Pro-D-Tyr-L-Arg amide

This peptide was synthesized as described in example 1 and prepared for use in the assay.

The inhibition of thrombin was determined by in-vitro inhibition of the amidase activity of the thrombin as in example 1 and is 47% with a peptide concentration of 1 µM.

EXAMPLE 11

N-acetyl-L-Ser-L-Arg-L-Cha-D-Pro-D-Tyr-L-Arg amide

This peptide was synthesized as described in example 1 and prepared for use in the assay.

The inhibition of thrombin was determined by in-vitro inhibition of the amidase activity of the thrombin as in example 1 and is 51% with a peptide concentration of 1 µM.

EXAMPLE 12

N-acetyl-D-Lys-L-Nle-L-Cha-D-Pro-D-Tyr-L-Arg amide

This peptide was synthesized as described in example 1 and prepared for use in the assay.

The inhibition of thrombin was determined by in-vitro inhibition of the amidase activity of the thrombin as in example 1 and is 48% with a peptide concentration of 1 µM.

EXAMPLE 13

N-acetyl-D-Tyr-L-Cha-D-Pro-D-Tyr-L-Arg amide

This peptide was synthesized as described in example 1 and prepared for use in the assay.

The inhibition of thrombin was determined by in-vitro inhibition of the amidase activity of the thrombin as in example 1 and is 47% with a peptide concentration of 1 µM.

EXAMPLE 14

N-acetyl-L-Arg-L-Cha-D-Pro-D-Tyr-L-Arg amide

This peptide was synthesized as described in example 1 and prepared for use in the assay.

The inhibition of thrombin was determined by in-vitro inhibition of the amidase activity of the thrombin as in example I and is 47% with a peptide concentration of 1 µM.

EXAMPLE 15

N-acetyl-L-Tyr-D-Pro-L-Cha-D-Pro-D-Tyr-L-Arg amide

This peptide was synthesized as described in example 1 and prepared for use in the assay.

The inhibition of thrombin was determined by in-vitro inhibition of the amidase activity of the thrombin as in example 1 and is 44% with a peptide concentration of 1 µM.

EXAMPLE 16

N-acetyl-L-Ala-D-Cha-L-Aze-D-Tyr-L-Arg amide

This peptide was synthesized as described in example 1 and prepared for use in the assay.

The inhibition of thrombin was determined by in-vitro inhibition of the amidase activity of the thrombin as in example 1 and is 63% with a peptide concentration of 1 µM.

EXAMPLE 17

N-acetyl-L-Ala-D-Cha-L-Pro-D-Tyr-L-Har amide

This peptide was synthesized as described in example 1 and prepared for use in the assay.

The inhibition of thrombin was determined by in-vitro inhibition of the amidase activity of the thrombin as in example 1 and is 56% with a peptide concentration of 1 µM.

EXAMPLE 18

N-acetyl-L-Trp-D-Cha-L-Aze-D-Tyr-L-Har amide

This peptide was synthesized as described in example 1 and prepared for use in the assay.

The inhibition of thrombin was determined by in-vitro inhibition of the amidase activity of the thrombin as in embodiment example 1 and is 76% with a peptide concentration of 250 nM.

EXAMPLE 19

N-acetyl-L-Ala-D-Cha-L-Aze-D-Tyr-L-Har amide

This peptide was synthesized as described in example 1 and prepared for use in the assay.

The inhibition of thrombin was determined by in-vitro inhibition of the amidase activity of the thrombin as in example 1 and is 77% with a peptide concentration of 250 nM.

EXAMPLE 20

N-acetyl-D-Phe-D-Cha-L-Aze-D-Tyr-L-Har amide

This peptide was synthesized as described in example 1 and prepared for use in the assay.

The inhibition of thrombin was determined by in-vitro inhibition of the amidase activity of the thrombin as in example 1 and is 77% with a peptide concentration of 250 nM.

EXAMPLE 21

N-acetyl-L-Dcp-D-Cha-L-Aze-D-Tyr-L-Har amide

This peptide was synthesized as described in example 1 and prepared for use in the assay.

The inhibition of thrombin was determined by in-vitro inhibition of the amidase activity of the thrombin as in example 1 and is 75% with a peptide concentration of 250 nM.

EXAMPLE 22

N-acetyl-L-Nhm-D-Cha-L-Aze-D-Tyr-L-Har amide

This peptide was synthesized as described in example 1 and prepared for use in the assay.

The inhibition of thrombin was determined by in-vitro inhibition of the amidase activity of the thrombin as in example 1 and is 80% with a peptide concentration of 250 nM.

EXAMPLE 23

N-acetyl-L-Iq3-D-Cha-L-Aze-D-Tyr-L-Har amide

This peptide was synthesized as described in example 1 and prepared for use in the assay.

The inhibition of thrombin was determined by in-vitro inhibition of the amidase activity of the thrombin as in example 1 and is 72% with a peptide concentration of 250 nM.

EXAMPLE 24

N-acetyl-L-Ppd-D-Cha-L-Aze-D-Tyr-L-Har amide

This peptide was synthesized as described in example 1 and prepared for use in the assay.

The inhibition of thrombin was determined by in-vitro inhibition of the amidase activity of the thrombin as in example 1 and is 76% with a peptide concentration of 250 nM.

EXAMPLE 25

N-acetyl-L-Tea-D-Cha-L-Aze-D-Tyr-L-Har amide

This peptide was synthesized as described in example 1 and prepared for use in the assay.

The inhibition of thrombin was determined by in-vitro inhibition of the amidase activity of the thrombin as in example 1 and is 74% with a peptide concentration of 250 nM.

EXAMPLE 26

N-acetyl-L-Phg-D-Cha-L-Aze-D-Tyr-L-Har amide

This peptide was synthesized as described in example 1 and prepared for use in the assay.

The inhibition of thrombin was determined by in-vitro inhibition of the amidase activity of the thrombin as in example 1 and is 95% with a peptide concentration of 250 nM.

EXAMPLE 27

N-acetyl-L-Nle-D-Cha-L-Aze-D-Tyr-L-Har amide

This peptide was synthesized as described in example 1 and prepared for use in the assay.

The inhibition of thrombin was determined by in-vitro inhibition of the amidase activity of the thrombin as in example 1 and is 75% with a peptide concentration of 250 nM.

EXAMPLE 28

N-acetyl-L-Cha-D-Cha-L-Aze-D-Tyr-L-Har amide

This peptide was synthesized as described in example 1 and prepared for use in the assay.

The inhibition of thrombin was determined by in-vitro inhibition of the amidase activity of the thrombin as in example 1 and is 89% with a peptide concentration of 250 nM.

EXAMPLE 29

N-acetyl-L-Pnp-D-Cha-L-Aze-D-Tyr-L-Har amide

This peptide was synthesized as described in example 1 and prepared for use in the assay.

The inhibition of thrombin was determined by in-vitro inhibition of the amidase activity of the thrombin as in example 1 and is 90% with a peptide concentration of 250 nM.

EXAMPLE 30

Tranexamic acid-D-Cha-L-Aze-D-Try-L-Har amide

This peptide was synthesized as described in example 1 and prepared for use in the assay. A $K_i$ of 7 nM was determined for the inhibition of the thrombin.

EXAMPLE 31

Trans-4-(guanidinomethyl)cyclohexanecarboxylic acid-D-Cha-L-Aze-D-Try-L-Har amide This peptide was synthesized as described in example 1 and prepared for use in the assay. A $K_i$ of 3 nM was determined for the inhibition of the thrombin.

DESCRIPTION OF THE ABBREVIATIONS

Ala=alanine
Val=valine
Leu=leucine
Ile=isoleucine
Pro=proline
Phe=phenylalanine
Phg=phenylglycine
Cha=cyclohexylalanine
Trp=tryptophan
Met=methionine
Gly=glycine
Ser=serine
Thr=threonine
Cys=cysteine
Tyr=tyrosine
Asn=asparagine
Gln=glutamine
Asp=aspartic acid
Glu=glutamic acid
Lys=lysine
Arg=arginine His=histidine
Nle=norleucine
Orn=ornithine
Cit=citrullin
Aze=azetidine
Har=homoarginine
Dcp=dichlorophenylalanine
Nhm=tetrahydronorhaman-3-carboxylic acid
Iq3=tetrahydroisoquinoline-(1,2,3,4)-3-carboxylic acid
Ppd=4-phenylpiperidine-4-carboxylic acid
Tea=thienylalanine
Pnp=paranitrophenylalanine $X^3$ is an L- or D-amino acid selected from the group consisting of Cha and Chg;

$X^4$ is an L- or D-amino acid selected from the group consisting of Pro and Aze (azetidine-2-carboxylic acid);

$X^5$ is an L- or D-amino acid selected from the group consisting of Tyr and Phe;

$X^6$ is an L- or D-amino acid selected from the group consisting of Arg, Lys, Orn, and Har; and $Y^2$ is a hydrogen, a hydroxyl, an amino, 7-amido-4-methylcoumarin, or paranitroanilide.

2. A compound according to claim 1, wherein $Y^2$ is 7-amido-4-methylcoumarin or paranitroanilide.

---

---

The invention claimed is:

1. A compound or pharmaceutically acceptable salt thereof of the formula

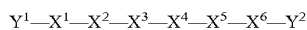

wherein
  $Y^1$ is a hydrogen, a methyl, an acetyl, or is characterized by a chain of 1 to 32 carbon atoms;
  $X^1$ is an L- or D-amino acid selected from the group consisting of tranexamic acid and trans-4-(guanidinomethyl) cyclohexanecarboxylic acid;
  $X^2$ is absent, or is an L- or D-amino acid selected from the group consisting of Ala, Val, Leu, Ile, Nle, Ser, Thr, Tyr, Pro, Cit, Arg, Lys, Orn, His, Glu, Asp, Trp, Cha (cyclohexylalanine), and Chg (cyclohexylglycine);

3. A compound according to claim 1, which is selected from the group consisting of
  N-Acetyl-$X^1$-$X^2$-L-Cha-D-Pro-D-Tyr-L-Arg-amide;
  N-Acetyl-D-Gln-D-His-L-Cha-D-Pro-D-Tyr-L-Arg-amide;
  N-Acetyl-D-Glu-L-Cha-D-Pro-D-Tyr-L-Arg-amide;
  N-Acetyl-D-Val-D-His-L-Cha-D-Pro-D-Tyr-L-Arg-amide;.
  N-Acetyl-L-Ala-L-Cha-D-Pro-D-Tyr-L-Arg-amide;
  N-Acetyl-L-Ile-L-Arg-L-Cha-D-Pro-D-Tyr-L-Arg-amide;
  N-Acetyl-L-Tyr-L-Cit-L-Cha-D-Pro-D-Tyr-L-Arg-amide;
  N-Acetyl-L-Ser-L-Ser-L-Cha-D-Pro-D-Tyr-L-Arg-amide;

N-Acetyl-D-Val-L-Cha-D-Pro-D-Tyr-L-Arg-amide;
N-Acetyl-L-Trp-L-Cha-D-Pro-D-Tyr-L-Arg-amide;
N-Acetyl-L-Ser-L-Ala-L-Cha-D-Pro-D-Tyr-L-Arg-amide
N-Acetyl-L-Ser-L-Arg-L-Cha-D-Pro-D-Tyr-L-Arg-amide
N-Acetyl-D-Lys-L-Nle-L-Cha-D-Pro-D-Tyr-L-Arg-amide;
N-Acetyl-D-Tyr-L-Cha-D-Pro-D-Tyr-L-Arg-amide;
N-Acetyl-L-Arg-L-Cha-D-Pro-D-Tyr-L-Arg-amide;
N-Acetyl-L-Tyr-D-Pro-L-Cha-D-Pro-D-Tyr-L-Arg-amide;
N-Acetyl-L-Ala-D-Cha-L-Aze-D-Tyr-L-Arg-amide;
N-Acetyl-L-Ala-D-Cha-L-Pro-D-Tyr-L-Har-amide;
N-Acetyl-L-Trp-D-Cha-L-Aze-D-Tyr-L-Har-amide;
N-Acetyl-L-Ala-D-Cha-L-Aze-D-Tyr-L-Har-amide;
N-Acetyl-D-Phe-D-Cha-L-Aze-D-Tyr-L-Har-amide;
N-Acetyl-L-Dcp-D-Cha-L-Aze-D-Tyr-L-Har-amide;
N-Acetyl-L-Nhm-D-Cha-L-Aze-D-Tyr-L-Har-amide;
N-Acetyl-L-Iq3-D-Cha-L-Aze-D-Tyr-L-Har-amide;
N-Acetyl-L-Ppd-D-Cha-L-Aze-D-Tyr-L-Har-amide;
N-Acetyl-L-Tea-D-Cha-L-Aze-D-Tyr-L-Har-amide;
N-Acetyl-L-Phg-D-Cha-L-Aze-D-Tyr-L-Har-amide;
N-Acetyl-L-Nle-D-Cha-L-Aze-D-Tyr-L-Har-amide;
N-Acetyl-L-Cha-D-Cha-L-Aze-D-Tyr-L-Har-amide;
N-Acetyl-L-Pnp-D-Cha-L-Aze-D-Tyr-L-Har-amide;
tranexamic acid-D-Cha-L-Aze-D-Tyr-L-Har-amide; and
trans-4-(guanidinomethyl)cyclohexanecarboxylic acid-D-Cha-L-Aze-D-Tyr-L-Har-amide.

4. A compound according to claim 1, where the compound is present as a pharmaceutically acceptable salt which is formed with and inorganic acid.

5. A compound of claim 4, wherein the inorganic acid is either
   i) hydrochloric acid, chloric acid, hydrobromic acid, bromic acid and/or another halogen acid; or
   ii) sulfuric acid and/or phosphoric acid.

6. A compound according to claim 1, where the compound is present as a pharmaceutically acceptable salt which is formed with an organic acid.

7. A compound according to claim 6, wherein the organic acid is acetic acid, propionic acid, malonic acid, maleic acid, citric acid, succinic acid, malic acid, benzoic acid, fumaric acid.

8. A composition comprising the compound of claim 1, and a pharmaceutically acceptable carner.

9. A composition comprising the compound of claim 2, and a pharmaceutically acceptable carrier.

10. A composition comprising the compound of claim 3, and a pharmaceutically acceptable carrier.

11. A composition of claim 8, further comprising carriers, adjuvants, or additives or combinations thereof.

12. A composition of claim 9, further comprising carriers, adjuvants, or additives or combinations thereof.

13. A composition of claim 10, further comprising carriers, adjuvants, or additives or combinations thereof.

14. A method of thrombin inhibition comprising administering to a human or animal in need thereof an effective amount of the composition of claim 8.

15. A method of thrombin inhibition comprising administering to a human or animal in need thereof an effective amount of the composition of claim 9.

16. A method of thrombin inhibition comprising administering to a human or animal in need thereof an effective amount of the composition of claim 10.

* * * * *

SEQUENCE LISTING

<160> NUMBER OF SEQ ID NOS: 3

<210> SEQ ID NO 1
<211> LENGTH: 4
<212> TYPE: PRT
<213> ORGANISM: artificial
<220> FEATURE:
<223> OTHER INFORMATION: synthetic protein

<400> SEQUENCE: 1

Phe Pro Arg Pro
1

<210> SEQ ID NO 2
<211> LENGTH: 4
<212> TYPE: PRT
<213> ORGANISM: artificial
<220> FEATURE:
<223> OTHER INFORMATION: synthetic protein

<400> SEQUENCE: 2

Gly Gly Gly Gly
1

<210> SEQ ID NO 3
<211> LENGTH: 12
<212> TYPE: PRT
<213> ORGANISM: Artificial
<220> FEATURE:
<223> OTHER INFORMATION: syntheitc protein

<400> SEQUENCE: 3

Asn Gly Asp Phe Glu Glu Ile Pro Gln Gln Tyr Leu
1               5                   10